(12) United States Patent
Kuen et al.

(10) Patent No.: US 6,264,642 B1
(45) Date of Patent: Jul. 24, 2001

(54) ELASTICIZED LAMINATE, LIQUID IMPERMEABLE BACKSHEET FOR A DISPOSABLE ABSORBENT ARTICLE

(75) Inventors: David Arthur Kuen, Neenah; John Irvin Van Deurzen, Menasha, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/609,139

(22) Filed: Feb. 29, 1996

(51) Int. Cl.$^7$ .................................................. A61F 13/15
(52) U.S. Cl. ........................... 604/385.28; 604/385.25; 604/385.76; 604/385.27; 604/385.29
(58) Field of Search ........................ 604/309, 373, 604/377, 378, 380, 384, 385.1, 385.2, 386, 387, 389, 390, 391, 393, 397, 398, 385.01, 385.101, 385.24–385.3

(56) References Cited

U.S. PATENT DOCUMENTS

| | | | |
|---|---|---|---|
| Re. 33,106 | 11/1989 | Beckestrom | 604/385.2 |
| 3,848,594 | * 11/1974 | Buell | 607/396 |
| 4,040,423 | 8/1977 | Jones, Sr. . | |
| 4,205,679 | * 6/1980 | Repke et al. | 607/394 |
| 4,425,127 | 1/1984 | Suzuki et al. | 604/366 |
| 4,490,148 | 12/1984 | Beckestrom | 604/385 |
| 4,601,717 | 7/1986 | Blevins . | |
| 4,657,539 | 4/1987 | Hasse . | |
| 4,681,579 | 7/1987 | Toussant et al. . | |
| 4,695,278 | 9/1987 | Lawson . | |
| 4,704,115 | 11/1987 | Buell . | |
| 4,704,116 | 11/1987 | Enloe . | |
| 4,711,683 | 12/1987 | Merkatoris | 156/164 |
| 4,738,677 | 4/1988 | Foreman . | |
| 4,743,246 | 5/1988 | Lawson . | |
| 4,795,452 | 1/1989 | Blaney et al. | 604/385.1 |
| 4,808,177 | 2/1989 | DesMarais et al. | 604/385.1 |
| 4,808,178 | 2/1989 | Aziz et al. | 604/385.2 |

(List continued on next page.)

FOREIGN PATENT DOCUMENTS

| | | |
|---|---|---|
| 0 386 815 | 9/1990 | (EP) . |
| 0 532 035 | 3/1993 | (EP) . |
| 0 549 988 | 7/1993 | (EP) . |
| 0 622 063 | 11/1994 | (EP) . |
| 0 625 346 | 11/1994 | (EP) . |
| 0 670 154 | 9/1995 | (EP) . |
| 2 262 873 | 7/1993 | (GB) . |
| 2 268 389 | 1/1994 | (GB) . |
| 94/18927 | 9/1994 | (WO) . |

OTHER PUBLICATIONS

Patent Cooperation Treaty Search Report from the International Search Authority, International Application No. PCT/US 97/01998 dated Jun. 27, 1997.

Primary Examiner—Glenn K. Dawson
Assistant Examiner—K. M. Reichle
(74) Attorney, Agent, or Firm—Thomas M. Gage; Douglas L. Miller

(57) ABSTRACT

A disposable absorbent article has a liquid impermeable backsheet, a liquid permeable topsheet, and an absorbent structure therebetween. The backsheet defines a liquid barrier zone on both sides of the absorbent structure, and a pair of liquid impermeable containment flaps overlie the liquid barrier zones. Leg elastic members are disposed along the side edges of the backsheet, and flap elastic members are disposed in the liquid impermeable containment flaps. A liquid barrier is in each liquid barrier zone, and extends between the front edge and back edge of the liquid impermeable backsheet. Each liquid barrier is desirably between a respective leg elastic member and flap elastic member.

21 Claims, 4 Drawing Sheets

U.S. PATENT DOCUMENTS

| | | | |
|---|---|---|---|
| 4,816,025 | 3/1989 | Foreman | 604/385.2 |
| 4,816,026 | 3/1989 | Richardson | 604/385.2 |
| 4,822,435 | 4/1989 | Igaue et al. | 156/164 |
| 4,834,740 | 5/1989 | Suzuki et al. | 604/385.2 |
| 4,846,823 | 7/1989 | Enloe | 604/385.2 |
| 4,846,825 | 7/1989 | Enloe et al. | 604/385.1 |
| 4,892,528 | 1/1990 | Suzuki et al. | 604/385.2 |
| 4,900,317 | 2/1990 | Buell | 604/370 |
| 4,904,251 | 2/1990 | Igaue et al. | 604/385.2 |
| 4,938,755 | 7/1990 | Foreman | 604/385.2 |
| 4,940,464 | 7/1990 | Van Gompel et al. | 604/396 |
| 5,021,051 | 6/1991 | Hiuke | 604/385.2 |
| 5,032,120 | 7/1991 | Freeland et al. | 604/385.2 |
| 5,046,272 | 9/1991 | Vogt et al. | 38/143 |
| 5,080,658 | 1/1992 | Igaue et al. | 604/385.2 |
| 5,087,255 | 2/1992 | Sims | 604/385.1 |
| 5,104,116 | 4/1992 | Pohjola | 271/185 |
| 5,114,420 | 5/1992 | Igaue et al. | 604/385.2 |
| 5,167,653 | 12/1992 | Igaue et al. | 604/385.2 |
| 5,188,627 | 2/1993 | Igaue et al. | 604/385.2 |
| 5,224,405 | 7/1993 | Pohjola | 83/24 |
| 5,403,301 * | 4/1995 | Huffman et al. | 604/385.2 |
| 5,415,644 | 5/1995 | Enloe | 604/385.2 |
| 5,575,785 | 11/1996 | Gryskiewicz et al. | 604/385.2 |

* cited by examiner

ELASTICIZED LAMINATE, LIQUID IMPERMEABLE BACKSHEET FOR A DISPOSABLE ABSORBENT ARTICLE

BACKGROUND OF THE INVENTION

The present invention relates to disposable absorbent articles, and more particularly to a disposable absorbent article having an elasticized laminate, liquid impermeable backsheet for improving waste containment.

Disposable absorbent products have been designed and used for various purposes. For example, some have been designed for use as diapers for babies, some as training pants for younger children generally between the age of 18 months to 36 months, and some as incontinence products for adults. One of the most important functions of any disposable absorbent product is the containment of liquid and other waste material. Failure to do so results in leakage and wetting of the clothes, both of which are highly undesirably to the wearers and caregivers.

Most of these disposable absorbent products are multi-layer designs having a liquid impermeable outer layer, a liquid permeable inner layer, and an absorbent therebetween. There may be additional components, such as containment flaps, additional layers of absorbent material, elastic materials, or the like. In many of these products, the sides or edges of some of the layers are coincident, and this can cause a problem in accurately registering or positioning other components relative to the coincident layers. This is due to the weaving of the layers as they proceed through the manufacturing process, and is generally termed "web weave." Other problems relating to this lack of web weave tolerance include inaccurate application of adhesive to or between layers or components, the necessity of applying excessive amounts of adhesive, or the like.

Ultimately, any one of these problems, or a combination, can cause undesired tearing or separation of layers or components in the products, increased cost in manufacture or materials, undesired exposure of layers or components, inferior waste containment, or the like. In view of this, it is apparent that there exists a need for improving waste containment.

SUMMARY OF THE INVENTION

In response to the discussed difficulties and problems encountered in the prior art, a disposable absorbent article having improved waste containment has been discovered.

In one form of the present invention there is provided a disposable absorbent article including a liquid impermeable backsheet and an absorbent structure on the backsheet. The liquid impermeable backsheet defines a liquid barrier zone on each side of its centerline, and both liquid barrier zones extend between a front edge and a back edge of the liquid impermeable backsheet. A liquid impermeable containment flap is over each liquid barrier zone, and a mechanism extends between the front edge and back edge of the backsheet in the liquid barrier zones to provide liquid barriers between the liquid impermeable containment flaps and the liquid impermeable backsheet.

In another form of the present invention there is provided a disposable absorbent article including a backsheet having an outer layer and a liquid impermeable inner layer. A leg elastic member is elastically associated along each side edge of the backsheet, and is positioned between the outer layer and the liquid impermeable inner layer. An absorbent structure is on the backsheet, and a liquid barrier zone is defined by the backsheet on each side of the absorbent structure, wherein both liquid barrier zones extend between a front edge and a back edge of the backsheet. A liquid impermeable containment flap is over each liquid barrier zone, and a liquid barrier is in each liquid barrier zone between the containment flap and the backsheet.

In still another form of the present invention there is provided a disposable absorbent article including a pant body having a waist opening periphery, a pair of leg opening peripheries, and an interior space. The pant body further includes a liquid impermeable backsheet having a front edge and a back edge that are substantially contiguous with the waist opening periphery. An absorbent structure is on the liquid impermeable backsheet in the interior space, and a liquid barrier zone is defined by the backsheet on each side of the absorbent structure. A liquid impermeable containment flap is over each liquid barrier zone, and a liquid barrier is in each liquid barrier zone between the liquid impermeable containment flap and the liquid impermeable backsheet.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DETAILED DESCRIPTION

The principles of the present invention can be incorporated into any suitable disposable absorbent article. Examples of such suitable articles include diapers for babies, training pants for children, and incontinence products for adults. For ease of explanation, the description hereafter will be in terms of a child's training pant.

Figure 1:
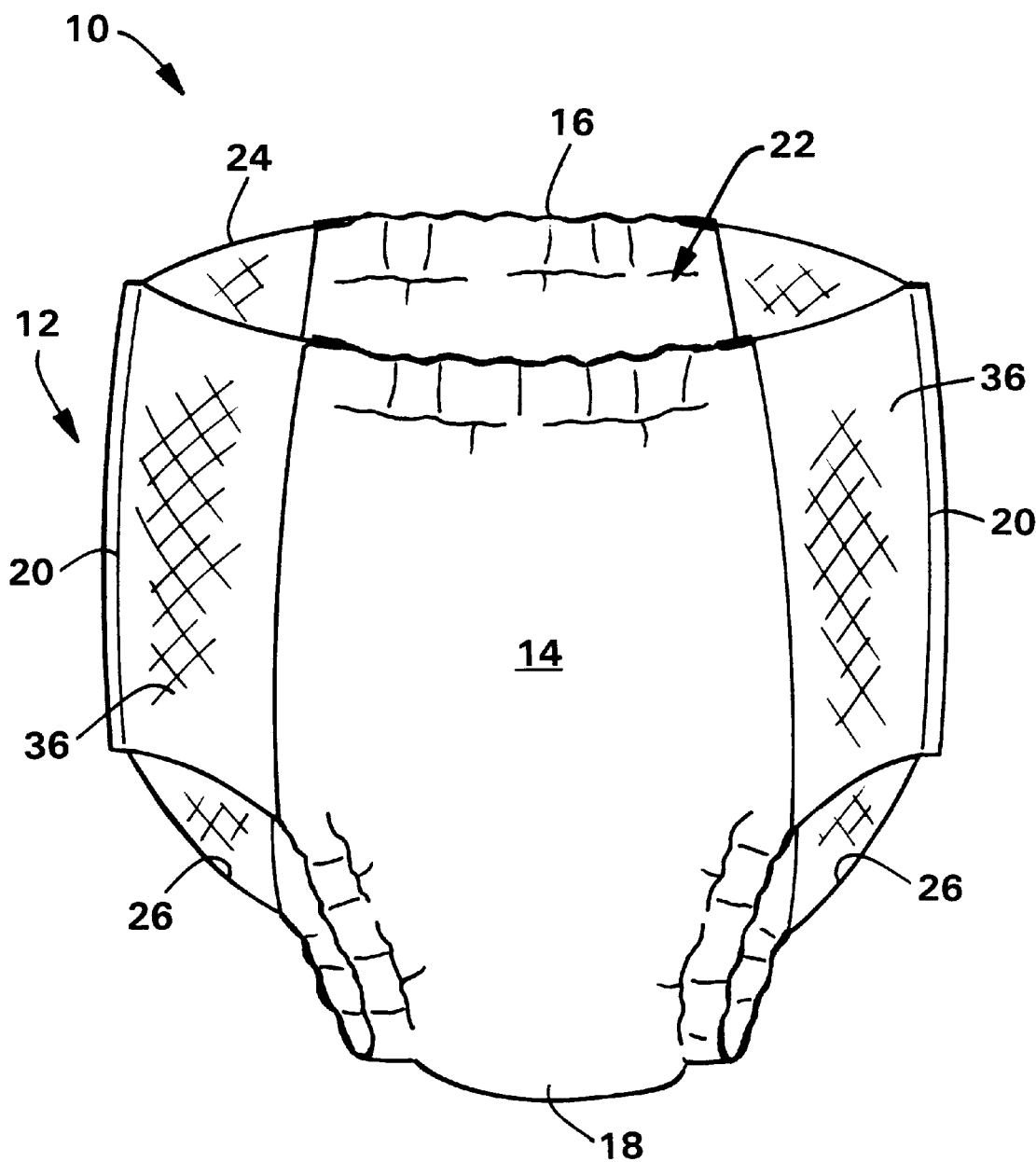
FIG. 1 illustrates a front perspective view of one type of disposable absorbent article incorporating the principles of the present invention.

Referring to FIG. 1, there is illustrated a disposable absorbent article, such as a training pant 10, comprising a pant body 12 including a front panel 14, a back panel 16, and a crotch panel 18 interconnecting front panel 14 with back panel 16. A pair of tearable, nonrefastenable side seams 20 join selected portions of front panel 14 and back panel 16 to define an interior space 22, a waist opening periphery 24, and a pair of leg opening peripheries 26. The term "disposable" means that the described article is designed to be used until soiled, either by urination, defecation, or otherwise, and then discarded rather than being washed and reused. The term "pant body" refers to an article that has a waist opening and a pair of leg openings similar to shorts, swim wear or the like.

Figure 2:
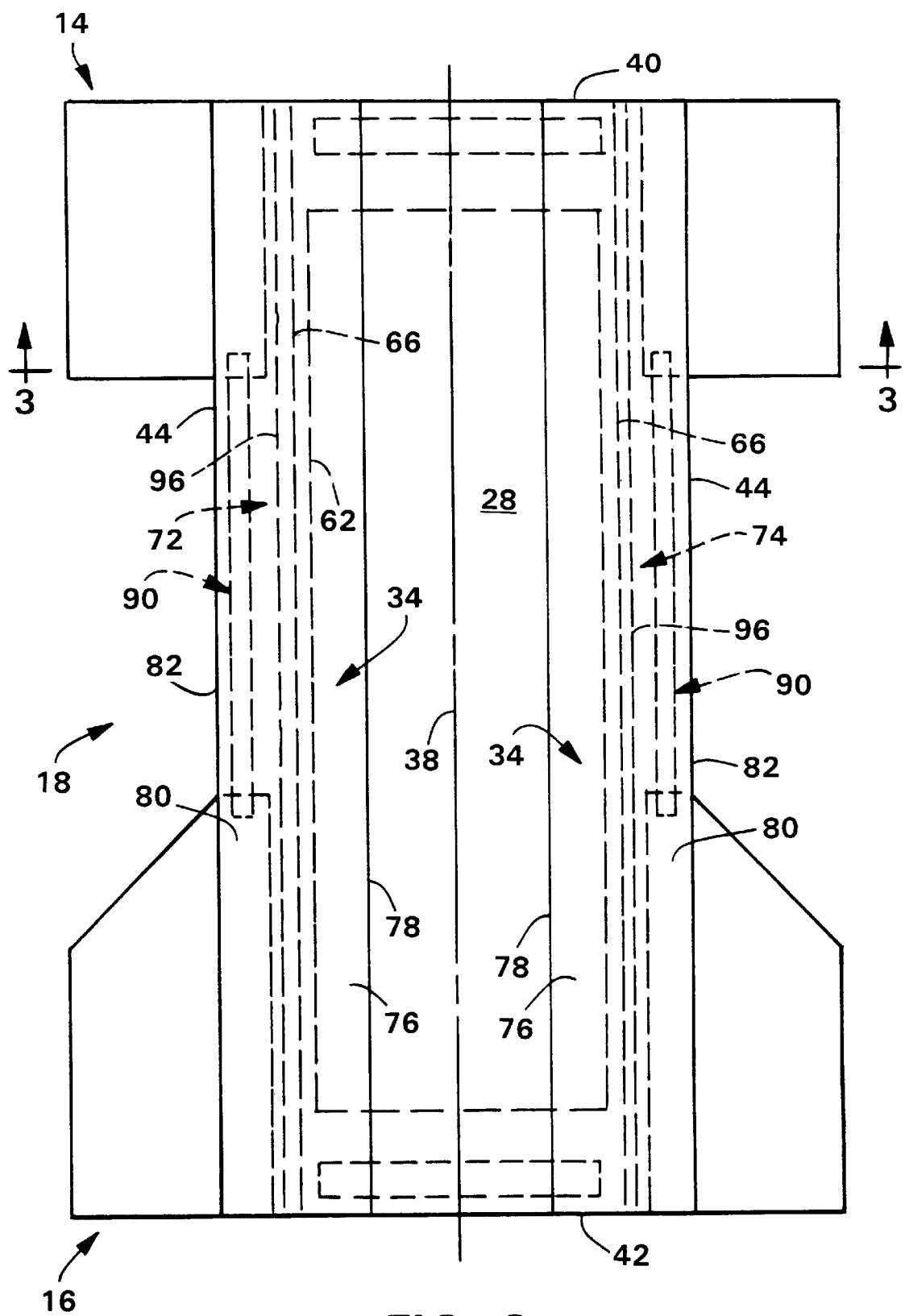
FIG. 2 illustrates a top plan, partially disassembled view of the article in FIG. 1.
Figure 3:
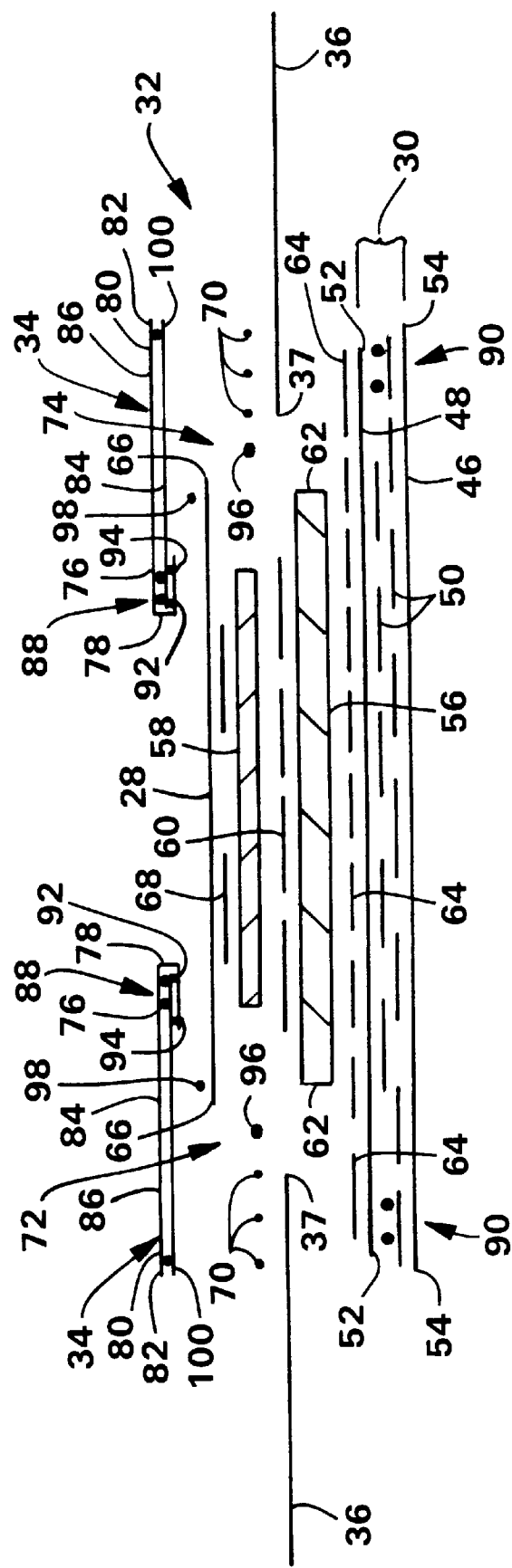
FIG. 3 illustrates an exploded, cross-sectional view of FIG. 2 taken along line 3—3 and viewed in the direction of the arrows.

Referring primarily to FIGS. 2–3, training pant 10 comprises in major part a liquid permeable topsheet 28, a liquid impermeable backsheet 30, an absorbent structure 32 between topsheet 28 and backsheet 30, a pair of liquid impermeable containment flaps 34, and elastic side panels 36. The liquid impermeable backsheet 30 desirably has a width greater than that of the liquid permeable topsheet 28, in which the width dimension is measured along a line perpendicular to centerline 38 (FIG. 2). Because the topsheet 28 is narrower than the backsheet 30, a portion or zone of the liquid impermeable backsheet 30, on each side of the absorbent structure 32, is exposed along the full length thereof, in which the length dimension is measured in a direction parallel to centerline 38. Generally, each exposed zone, hereinafter referred to as a liquid barrier zone, has a width of about 2 millimeters or greater, a desired width of about 4 millimeters or greater, and a more desired width of about 6 millimeters or greater.

With reference to FIG. 3, backsheet 30 is illustrated wider than topsheet 28, which noticeably compares with those current disposable absorbent products that have their various layers generally coincident. In these current products, there is very little, if any, tolerance for web weave, which is the uncontrolled, erratic movement of a layer or web as it continuously moves at high speeds through a manufacturing process. Although various devices, such as dancer roles, feed controls, and the like, have been used to minimize web weave, there is still a measurable amount of undesirable weave in those processes. With current disposable absorbent products, because the layers are coincident, or at least very close together along their sides or edges, this low tolerance for web weave results in adhesive lines being applied outside of their desired positions, such that they may adhere wrong components together, or fail to adhere the correct components together.

As illustrated in FIG. 3, one of the advantages of the present invention is the exposed liquid barrier zones between the topsheet 28 and backsheet 30 that provide increased tolerances for accommodating web weave, thereby improving processability in the manufacturing process. This web weave tolerance can be further increased by eliminating topsheet 28 in those disposable absorbent articles that do not necessarily require a topsheet. Due to the increased web weave tolerance, components now have a wider attachment or positioning area. For example, since backsheet 30 is relatively wider, the elastic side panels 36 can now be spaced farther apart in the width direction. This permits the elastic side panels 36 to be made more narrow in width, since they now are spaced farther apart on either side 62 of absorbent structure 32. This results in a significant reduction in cost, since the materials of which elastic side panels 36 are made are expensive compared to the other materials in training pant 10.

The increased web weave tolerance also provides wider areas of application of bondlines for joining various components together. This greatly minimizes or eliminates a bondline failing to join the correct components together, or undesirably joining wrong components together.

Still another advantage of the present invention is that a wider absorbent structure 32 can be placed with a wider backsheet 30, thereby providing increased absorbent capacity. These advantages, along with others, will be described in greater detail hereafter.

The liquid impermeable backsheet 30 has a front edge 40 (FIG. 2) substantially contiguous with waist opening periphery 24 (FIG. 1), a back edge 42 substantially contiguous with waist opening periphery 24, and a pair of side edges 44. The term "liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein. Backsheet 30 can be a single layer of liquid impermeable material, or can be a multi-layered laminate structure in which at least one of the layers is impermeable to liquid. As illustrated in FIG. 3, liquid impermeable backsheet 30 includes a liquid permeable outer layer 46 and a liquid impermeable inner layer 48 that are suitably joined together by a laminate adhesive 50. Laminate adhesive 50 can be applied continuously or intermittently as beads, a spray, parallel swirls, or the like. Suitable adhesives can be obtained from Findley Adhesives, Inc., of Wauwatosa, Wis., or from National Starch and Chemical Company, Bridgewater, N.J. Liquid permeable outer layer 46 can be any suitable material that provides a generally cloth-like texture. One example of such a material is a 20 gsm (grams per square meter) spunbond polypropylene nonwoven web. Outer layer 46 may also be made of those materials of which liquid permeable topsheet 28 is made. Further, it is not a necessity for outer layer 46 to be liquid permeable, but it is desired that it provides a relatively cloth-like texture to the wearer.

The inner layer 48 of backsheet 30 can be both liquid and vapor impermeable, or can be liquid impermeable and vapor permeable. Inner layer 48 is desirably manufactured from a thin plastic film, although other flexible liquid impermeable materials may also be used.

Inner layer 48, or liquid impermeable backsheet 30 when a single layer, prevents waste material from wetting articles, such as bedsheets and clothing, as well as the wearer and caregiver. A suitable liquid impermeable film for use as liquid impermeable inner layer 48, or a single layer liquid impermeable backsheet 30, is a 1.0 mil polyethylene film commercially available from Edison Plastics Company of South Plainfield, N.J. If backsheet 30 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the backsheet 30. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

When backsheet 30 is a multi-layer laminate, as is illustrated in FIG. 3, liquid impermeable inner layer 48 includes a pair of side edges 52, and outer layer 46 includes a pair of side edges 54. As illustrated in FIG. 3, side edges 52 are inboard of side edges 54, wherein "inboard" or "outboard" is with reference to centerline 38. In this instance, side edges 52 of liquid impermeable inner layer 48 correspond to side edges 44 (FIG. 2) of a single layer liquid impermeable backsheet 30. Both side edges 52 and side edges 54 can be contiguous, but this is not a requirement of the present invention.

Referring to FIGS. 1 and 3, absorbent structure 32 is positioned on backsheet 30 within interior space 22 of training pant 10. Absorbent structure 32 can include an absorbent pad 56 and a surge layer 58 suitably joined together, such as by topsheet adhesive 60.

Topsheet adhesive 60 can be any suitable adhesive applied in any manner well known in the art. Examples of suitable adhesives are the same as those with reference to laminate adhesive 50. Absorbent pad 56 can be any structure which is generally compressible, conformable, nonirritating to the child's skin, and capable of absorbing and retaining liquids and certain body wastes. Absorbent pad 56 can be manufactured in a wide variety of sizes and shapes, and from a wide variety of liquid absorbent materials commonly used in the art. For example, absorbent pad 56 can comprise pulp fluff, superabsorbent material, or a combination of both. If in combination, the pulp fluff and the superabsorbent material can be blended together, or can comprise discrete layers of fluff and discrete layers of superabsorbent material. Various types of wettable, hydrophilic fibrous material include naturally occurring organic fibers composed of intrinsically wettable materials, such as cellulosic fibers; synthetic fibers composed of cellulose or cellulose derivatives, such as rayon fibers; inorganic fibers composed of an inherently wettable material, such as glass fibers; and synthetic fibers composed of a nonwettable, thermoplastic polymer, such as polypropylene fibers that have been hydrophilized by appropriate means, such as by treatment with silica, treatment with a material which has a suitable hydrophilic moiety, or the like.

Suitable superabsorbent materials may be organic or inorganic. Suitable inorganic superabsorbent materials include, by way of example, absorbent clays and silica gels. Other suitable superabsorbent materials are available from various commercial vendors, such as Dow Chemical Company, Hoechst-Celanese Corporation, and Allied Colloids, Inc. Typically, a superabsorbent material is capable of absorbing at least about 15 times its weight in water, and desirably is capable of absorbing more than about 25 times its weight in water.

In one embodiment, absorbent pad 56 is generally rectangular in shape, and comprises a blend of wood pulp fluff and superabsorbent material. One preferred type of fluff is identified with the trade designation CR1654, available from Kimberly-Clark Corporation, Neenah, Wis., and is a bleached, highly absorbent sulfate wood pulp containing primarily soft wood fibers. The fluff and superabsorbent material in absorbent pad 56 are present in a ratio of about 9 grams to about 20 grams fluff, to about 7 grams to about 14 grams superabsorbent material. The absorbent pad 56 has a density within the range of about 0.10 grams per cubic centimeter to about 0.35 grams per cubic centimeter. The absorbent pad 56 may or may not be wrapped or encompassed by a suitable tissue wrap that maintains the integrity and/or shape of absorbent pad 56.

Surge layer 58 is constructed and designed primarily to receive, temporarily store, and transport liquid along the mutually facing surface with absorbent pad 56, thereby maximizing the absorbent capacity of absorbent structure 32. One suitable construction and design of a surge layer 58 is a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese.

Absorbent structure 32 is suitably joined to backsheet 30 by construction adhesive 64. Construction adhesive 64 can, as with laminate adhesive 50, be any suitable adhesive applied in any manner well known in the art.

Referring to FIGS. 2 and 3, liquid permeable topsheet 28 is illustrated as overlying backsheet 30 and absorbent structure 32. Liquid permeable topsheet 28 includes a pair of lateral edges 66 (FIG. 2) that are inboard of, i.e., nearer to centerline 38 than, side edges 44 of backsheet 30. Topsheet 28 is desirably compliant, soft feeling, and nonirritating to the child's skin, and permits liquids to readily penetrate through its thickness. Topsheet 28 may be manufactured from a wide range of materials, such as porous foams, reticulated foams, apertured plastic films, natural fibers, synthetic fibers, or from a combination of natural and synthetic fibers. If topsheet 28 comprises substantially hydrophobic material, the hydrophobic material can be treated with a surfactant or otherwise processed in order to impart a desired level of wettability and hydrophilicity. One such surfactant is a 0.28 percent TRITON X-102 surfactant. A suitable liquid permeable topsheet 28 is a nonwoven bicomponent web having a basis weight of about 27 gsm. The nonwoven bicomponent may be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. Topsheet 28 is suitably joined to absorbent pad 56 by topsheet adhesive 60, and is suitably joined to surge layer 58 by surge adhesive 68. These adhesives can be the same type of adhesive as that used for laminate adhesive 50.

As illustrated in FIG. 1, training pant 10 has an elastic side panel 36 disposed on each side thereof. Each elastic side panel 36 includes a seam 20 that ultrasonically bonds the two portions that form each elastic side panel 36. With reference to FIG. 3, each elastic side panel 36 is suitably joined to backsheet 30 by construction adhesive 64, and is suitably joined to a respective containment flap 34 by flap panel adhesive 70. As illustrated in FIG. 3, each flap panel adhesive 70 comprises three beads, or lines, of a suitable adhesive for joining each elastic side panel 36 to its respective containment flap 34. Use of the term "respective" describes a specific positional relationship between two elements; for example, in FIG. 3, elastic side panel 36 on the left-hand side of FIG. 3 is joined to a "respective" containment flap 34 on the same side of FIG. 3. Similar use of the term "respective" in relation to other components, such as adhesives, elastic members, or the like, has the same meaning.

Suitable materials of which elastic side panels 36 can be made, as well as one described process of incorporating elastic side panels 36 into a training pant 10, are described in (i) U.S. Pat. No. 4,940,464, issued Jul. 10, 1990; (ii) U.S. Pat. No. 5,224,405, issued Jul. 6, 1993; (iii) U.S. Pat. No. 5,104,116, issued Apr. 14, 1992, and (iv) U.S. Pat. No. 5,046,272, issued Sep. 10, 1991; all of these aforementioned U.S. patents being incorporated by reference herein.

With reference to FIG. 3, a first liquid barrier zone 72 is positioned on one (the left) side of centerline 38 (FIG. 2), and a second liquid barrier zone 74 is formed on an other (the right) side of centerline 38. More specifically, first liquid barrier zone 72 is on one side of absorbent structure 32, and second liquid barrier zone 74 is on an other side of absorbent structure 32, wherein each liquid barrier zone 72, 74 is respectively defined by liquid impermeable backsheet 30. More specifically, each liquid barrier zone 72, 74 is defined, in the width dimension, by a respective side edge 52 of liquid impermeable inner layer 48 and a respective topsheet lateral edge 66 in crotch panel 18 (FIG. 2), and by a side edge 66 and a side edge 37 of an elastic side panel 36 in front and back panels 14, 16 (FIG. 2). Each liquid barrier zone 72, 74 is thus a defined exposed area of liquid impermeable backsheet 30, and extends between backsheet front edge 40 and backsheet back edge 42 (FIG. 2).

The width of liquid barrier zones 72, 74 is important to the present invention in that each liquid barrier zone 72, 74 should have sufficient width for the particular absorbent article design to provide the desired web weave tolerance earlier discussed. Each liquid barrier zone 72, 74 has a width of about 2 millimeters or greater, a desired width of about 4 millimeters or greater, and a more desired width of about 6 millimeters or greater. It also may be desired that a respective width of each liquid barrier zone 72, 74 be relatively constant between front edge 40 and back edge 42. However, it is within the scope of the present invention to permit the width of liquid barrier zones 72, 74 to vary within the previously described ranges. Finally, and with particular reference to FIG. 3, it is desired that a portion of construction adhesive 64 be placed or applied along the length in each liquid barrier zone 72, 74.

It is to be emphasized that there are no specific structures that must define liquid barrier zones 72, 74. For example, it is not a requirement that topsheet 28 should define, with backsheet 30, the liquid barrier zones 72, 74. It may be that a particular design and construction of a disposable absorbent article does not require a topsheet 28, and thus will permit liquid barrier zones 72, 74 to be defined or formed just by the lateral extension of a backsheet 30 beyond side edges 62 of an absorbent structure 32. The present invention includes any combination of various positional relationships of structural elements that define or form the liquid barrier zones 72, 74.

Continuing primarily with FIG. 3, a liquid impermeable containment flap 34 is over first liquid barrier zone 72, and another liquid impermeable containment flap 34 is over second liquid barrier zone 74. Furthermore, each liquid impermeable containment flap 34 desirably extends the full length and width of its respective liquid barrier zone 72, 74. Since liquid impermeable containment flaps 34 are substantially the same, a description of the left containment flap 34 in FIG. 3 will be made. Liquid impermeable containment flap 34, as just described, has a width that desirably exceeds that of liquid barrier zone 72, i.e., has an edge 78 that desirably extends inwardly of, with respect to centerline 38 (FIG. 2), topsheet lateral edge 66, and an edge 82 that desirably extends outwardly of side edge 52. Similarly, liquid impermeable containment flap 34 desirably extends the full length of liquid barrier zone 72 between front edge 40 and back edge 42 of backsheet 30.

Liquid impermeable containment flap 34 includes an inner portion 76 having an inner edge 78, and an outer portion 80 having an outer edge 82. Select areas of inner portions 76 of containment flaps 34 are attached to topsheet 28, adjacent front edge 40 and back edge 42 of backsheet 30. Each liquid impermeable containment flap 34 further includes a liquid impermeable inner layer 84, and an outer layer 86, which may or may not be liquid impermeable. Generally, outer layer 86 will be a liquid permeable material. Liquid impermeable inner layer 84 can be vapor permeable or vapor impermeable, and may be made of the same materials as inner layer 48 of backsheet 30. Similarly, outer layer 86 can be made of the same materials as outer layer 46 of backsheet 30. However, if desired, each containment flap 34 can be a single layer of a suitable liquid impermeable material. Generally, the choice of materials will be dictated by the manufacturing process and/or design of the absorbent article. A more detailed description of various containment flap designs and attachments are included in U.S. Pat. No. 5,415,644 issued May 16, 1995, the contents of which are incorporated by reference herein.

A flap elastic member 88 is elastically associated with each containment flap 34. In a specific embodiment, flap elastic member 88 is between liquid impermeable inner layer 84 and outer layer 86 at inner portion 76 of a respective containment flap 34. The term "elastically associated" refers to the joining of an elastic member to a non-elastic member such that the two joined members exhibit elasticity. The terms "elastic" and "elasticity" have the conventional meaning in the art, which refers to a material or composite elastic material that tends to recover its original, relaxed size and shape after removal of the force causing the deformation. Elasticity is expressed in percent. The term "member" when used in the singular can have the dual meaning of a single element or a plurality of elements.

Each flap elastic member 88 in a respective containment flap 34 can be joined or attached in any suitable manner well known in the art. For example, a flap elastic member 88 can be stretched and then adhered to either one or both inner layer 84 and outer layer 86. The adhesive used to join or adhere flap elastic member 88 in containment flap 34 can be applied continuously or intermittently. One suitable method of applying adhesive is by slot coating. Another suitable method is that described in U.S. Pat. No. 4,711,683 issued Dec. 8, 1987, the contents of which are incorporated by reference herein.

A leg elastic member 90 is elastically associated along each side edge 44 of backsheet 30. When backsheet 30 is a two-layer laminate structure, each leg elastic member 90 is desirably positioned between outer layer 46 and inner layer 48. Each leg elastic member 90 can be adhered to either or both outer layer 46 or inner layer 48, and in a manner similar to that of a flap elastic member 88 in a containment flap 34. Both the flap elastic members 88 and leg elastic members 90 can be made of any suitable elastic material, and one suitable material and construction is a plurality of strands of LYCRA 940 decitex that are joined to their respective layer, or layers, while at an elongation in the range of about 100% to about 400%. Each individual strand is spaced from an adjacent strand by about 3 millimeters. These types of elastic strands are commercially available from E. I. DuPont de Nemours Company, Wilmington, Del. Other suitable elastic materials include natural rubber, synthetic rubber, or thermoplastic elastomeric polymers. These elastic materials may also be heat-elasticizable, and can be single or multiple ribbons or strands of elastic material.

Continuing the description of a flap elastic member 88, each is desirably positioned between inner layer 84 and outer layer 86 at inner portion 76, and adjacent a respective inner edge 78. As illustrated in FIG. 3, there is a folded portion 92 of outer layer 86 that is folded or wrapped over a flap elastic member 88 and then positioned underneath, as viewed in FIG. 3, inner layer 84, such that inner layer 84 is sandwiched between folded portion 92 and outer layer 86. Folded portion 92 is then suitably adhered to inner layer 84 by adhesive bondline 94, which can be any suitable adhesive applied in any known manner in the art.

Important to the present invention is a means for providing a liquid barrier between liquid impermeable containment flaps 34 and liquid impermeable backsheet 30, in which the means extends between front edge 40 and back edge 42 of backsheet 30. In one embodiment, such a means is a liquid barrier 96 in each respective liquid barrier zone 72, 74, and which extends between front edge 40 and back edge 42. The liquid barrier 96 in each liquid barrier zone 72, 74 can be any suitable means or mechanism that provides obstruction to the passage or flow of liquid between a liquid impermeable containment flap 34 and liquid impermeable backsheet 30. Examples of this feature include, but are not limited to, an adhesive bondline, a thermal bondline, an ultrasonic bondline, or the like, and including combinations thereof. An adhesive bondline forming or defining a liquid barrier 96 can be applied in any suitable manner and in any pattern sufficiently to prevent or obstruct the passage of liquid, such as urine, between a containment flap 34 and backsheet 30 in a respective liquid barrier zone 72, 74. A thermal bondline forming or defining a liquid barrier 96 can be provided in any suitable manner that appropriately heats a liquid impermeable containment flap 34 and liquid impermeable backsheet 30 to make them sufficiently tacky, so that they can adhere together in a respective liquid barrier zone 72, 74. This assumes the containment flap 34 and backsheet 30 are thermally compatible. If not, then another layer of material, which is thermally compatible to both, can be positioned between a containment flap 34 and backsheet 30, and then all three thermally bonded together sufficiently to obstruct the passage of liquid. Similarly, an ultrasonic bondline forming or defining liquid barrier 96 can also be provided in any suitable manner and in any suitable pattern sufficiently to obstruct the passage of liquid. Suitable ultrasonic apparatus for providing an ultrasonic bondline are commercially available from Branson Ultrasonics Corporation, Danbury, Connt. If desired, a liquid barrier 96 can include a combination of these, or other, means for providing obstruction of liquid flow. For example, a liquid barrier 96 could include an adhesive bondline in the area of crotch panel 18 (FIG. 2), and a thermal bond pattern in the areas of front and back panels 14, 16 (FIG. 2).

A desirable feature of the present invention is that each liquid barrier 96 directly joins liquid impermeable backsheet 30 and a liquid impermeable containment flap 34. In other words, it is desirable that no other layer or substrate be between backsheet 30 and a containment flap 34 that would provide a potential defect in or failure of a liquid barrier 96 in obstructing the passage of liquid between backsheet 30 and a containment flap 34. For example, if topsheet 28 is increased in width so as to extend beyond the outermost portion of a liquid barrier zone 72, 74, a liquid barrier 96 could potentially fail to obstruct the passage of liquid between backsheet 30 and a containment flap 34. Thus, the desirability of topsheet 28 being narrower than backsheet sheet 30, such that lateral edges 66 (FIG. 2) are closer to centerline 38 than side edges 44 of backsheet 30. This desirability similarly applies to elastic side panels 36, absorbent pad 56, surge layer 58, or any other components of training pant 10.

As thus described, a liquid barrier 96 desirably provides a direct, mutually contacting joinder between liquid impermeable backsheet 30 and a respective liquid impermeable containment flap 34 to obstruct the passage of liquid through a barrier zone 72, 74. Parenthetically, and as illustrated in FIG. 3, when backsheet 30 is a multi-layer structure, and when liquid impermeable containment flaps 34 are multilayer structures, a liquid barrier 96 directly joins liquid impermeable inner layer 48 of backsheet 30 to liquid impermeable inner layer 84 of a respective containment flap 34.

Nevertheless, the present invention does include embodiments in which a component can be positioned in a liquid barrier zone 72, 74. For example, topsheet 28 can have its lateral edges 66 extend over a respective liquid barrier zones 72, 74. In this case, it is important that each liquid barrier zone 96 be suitably provided to accommodate the existence of this additional component, such as, for example, topsheet 28, in order to ensure the obstruction of liquid flow through liquid barrier zones 72, 74. If, for example, liquid barriers 96 are adhesive bondlines, then it is important that the adhesive material be selectively chosen and appropriately applied by a method and in an amount to create the desired obstruction of liquid flow.

Each liquid impermeable containment flap 34 is suitably adhered on top of topsheet 28, for example, by a respective flap seam 98. Flap seam 98 is desirably an adhesive bondline joining an intermediate portion of a containment flap 34 to topsheet 28. The height of a containment flap 34, as measured in a horizontal direction in FIG. 3, is then measured between a flap seam 98 and an inner edge 78. Each containment flap 34 is elastically urged upwardly, relative to topsheet 28, under the elastic tension of a respective flap elastic member 88. One suitable design and construction of a containment flap is set forth in U.S. Pat. No. 4,704,116 issued Nov. 3, 1987, the contents of which are incorporated by reference herein. Since one of the objectives of containment flaps 34 is to impede the flow of urine, or other waste material, and allow absorption thereof, each flap seam 98 is desirably positioned over absorbent structure 32 in order to enhance absorption. Thus, any urine or other flowable waste matter that moves or wicks underneath a flap seam 98 can still be absorbed by that portion of absorbent structure 32, such as absorbent pad 56, that extends outwardly beyond a respective flap seam 98.

The relative position of each flap seam 98 is important to the performance of the present invention. For example, it is desired that each flap seam 98 be disposed or positioned between a respective flap elastic member 88 and leg elastic member 90. The term "disposed or positioned between" means that flap seam 98 is "horizontally" disposed or positioned, as viewed in FIG. 3. In other words, it is not required that the flap elastic member 88, flap seam 98, and leg elastic 90 be positioned in a common plane. They can be vertically displaced relative to each other as is illustrated in FIG. 3. With a flap seam 98 intermediately positioned between a flap elastic member 88 and a leg elastic member 90, it will not enhance or affect the elasticity of one elastic member 88, 90 at the expense of the other. For example, if a flap seam 98 is immediately adjacent a flap elastic member 88, the elasticity of flap elastic member 88 could be diminished due to the presence of the adhesive associated with a flap seam 98.

If, however, the particular design and construction of a disposable absorbent article permits, flap seams 98 can be eliminated, and liquid barriers 96 can provide the additional feature of joining containment flaps 34 to backsheet 30, or topsheet 28 if it extends laterally a sufficient distance.

Similarly, each liquid barrier 96 is also desirably disposed or positioned between a respective leg elastic member 90 and a respective flap member 88, as illustrated in FIG. 3.

Continuing to refer to FIG. 3, each liquid impermeable containment flap 34 includes a flap construction adhesive 100 that adhesively joins flap inner layer 84 to flap outer layer 86 adjacent a respective flap outer edge 82. The purpose of each flap construction adhesive 100 includes joining the layers together for better performance, better aesthetics, easier processing during manufacture, and the like.

Although FIG. 3 illustrates flap construction adhesive 100 as a single bead or line of adhesive applied near outer edge 82 of flap 34, the flap construction adhesive 100 can be a series of parallel swirls of adhesive. In this case, it is desirable that each flap construction adhesive 100 is outboard of both a respective leg elastic member 90, liquid barrier 96, and flap elastic member 88.

Figure 4:
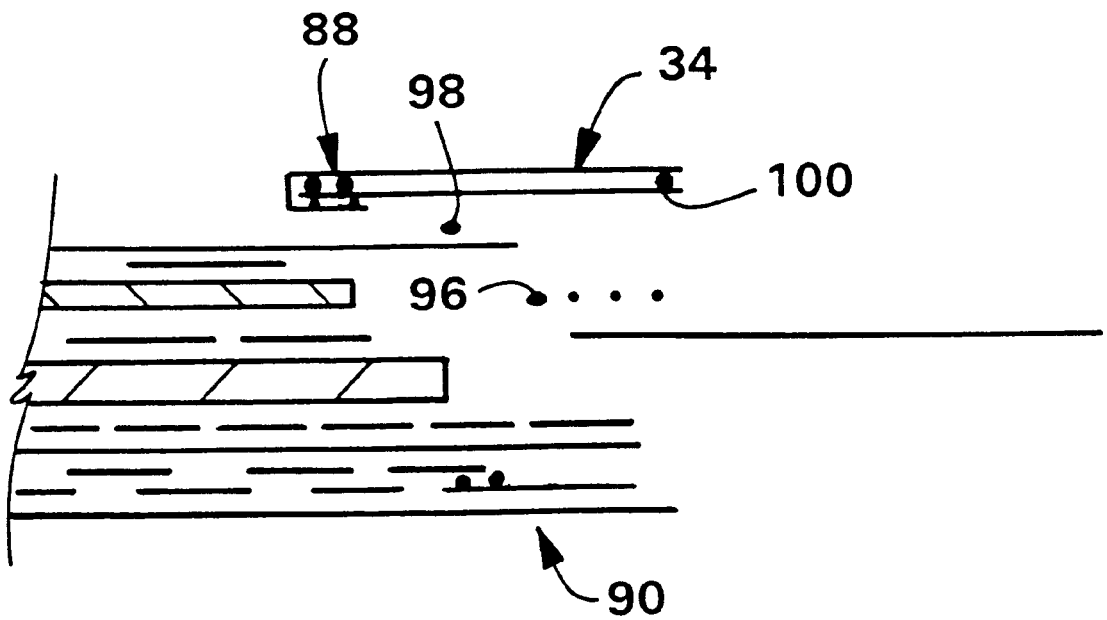
FIG. 4 illustrates a fragmentary view of a modification of the view in FIG. 3.

Turning now to FIG. 4, there is illustrated a fragmentary view of a modification, in which both a respective leg elastic member 90 and flap elastic member 88 are placed inboard of a respective liquid barrier 96. One reason for this can be due to a particular product design and construction, for example, where the absorbent structure 32 is shaped narrower at the crotch, and the leg elastic members 90 are curved to match, or generally parallel, the shape of the absorbent structure.

Figure 5:
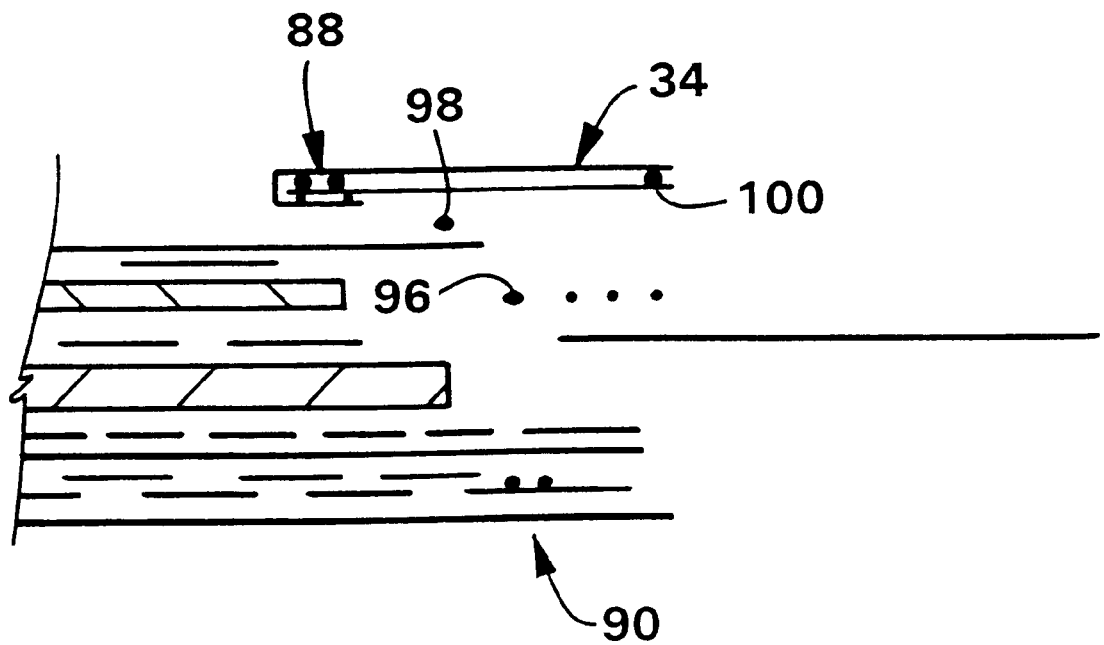
FIG. 5 illustrates a fragmentary view of another modification of the view in FIG. 3.

In FIG. 5, another modification is illustrated in which each leg elastic member 90 is also positioned in a respective liquid barrier zone 72, 74 along with the respective liquid barrier 96. One reason for this can be to increase or maximize the elastic effects of leg elastic members 90, since there is less material, i.e., layers of material, that the leg elastic members 90 must gather.

While this invention has been described as having a preferred embodiment, it will be understood that it is capable of further modifications. This application is therefore intended to cover any variation, equivalence, use, or adaptation of the invention following the general principles thereof, and including such departures from the present disclosure as come or may come within known or customary practice in the art to which this inventions pertains and fall within the limits of the appended claims.

What is claimed is:

1. A disposable absorbent article, comprising:
   a liquid impermeable backsheet comprising a front edge, a back edge, and a centerline extending between said front edge and said back edge,
   a liquid permeable topsheet,
   an absorbent structure between said liquid impermeable backsheet and said liquid permeable topsheet,
   a first liquid barrier zone defined on one side of said centerline, and a second liquid barrier zone defined on an other side of said centerline, said liquid barrier zones extending between said front edge and said back edge of said backsheet,
   a liquid impermeable containment flap over each said liquid barrier zone,
   a flap seam positioned over said absorbent structure and adhering said liquid impermeable containment flap on top of said liquid permeable topsheet, and
   means extending between said front edge and said back edge in said liquid barrier zones for providing liquid barriers between said liquid impermeable containment flaps and said liquid impermeable backsheet.

2. The article of claim 1 wherein each said containment flap includes an inner portion having a flap elastic member elastically associated therewith, and wherein said flap seam is between said providing means and said flap elastic member.

3. The article of claim 2 wherein said backsheet comprises an outer layer, a liquid impermeable inner layer, and a pair of side edges, and
   further comprising a leg elastic member elastically associated along each said side edge and positioned between said outer layer and said liquid impermeable inner layer.

4. The article of claim 3 wherein said providing means is between said leg elastic member and said flap elastic member.

5. The article of claim 4 wherein each said leg elastic member is in a respective said liquid barrier zone.

6. The article of claim 1 wherein each said containment flap is joined to said article by said providing means.

7. A disposable absorbent article, comprising:
   a backsheet comprising an outer layer, a liquid impermeable inner layer, a front edge, a back edge, and a pair of side edges,
   a leg elastic member elastically associated along each said side edge and positioned between said outer layer and said liquid impermeable inner layer,
   a topsheet,
   an absorbent structure between said backsheet and said topsheet,
   a first liquid barrier zone defined by said backsheet on one side of said absorbent structure, and a second liquid barrier zone defined by said backsheet on an other side of said absorbent structure, said liquid barrier zones extending between said front edge and said back edge of said backsheet,
   a liquid impermeable containment flap over each said liquid barrier zone,
   a flap seam Positioned over said absorbent structure and adhering said liquid impermeable containment flap on top of said topsheet, and
   a liquid barrier in each said liquid barrier zone between a respective said containment flap and said backsheet, and extending between said front edge and said back edge of said backsheet.

8. The article of claim 7 wherein each said liquid barrier comprises an adhesive bondline.

9. The article of claim 7 wherein each said liquid barrier comprises a thermal bondline.

10. The article of claim 7 wherein each said liquid barrier comprises an ultrasonic bondline.

11. The article of claim 7 wherein each said containment flap includes a flap elastic member elastically associated therewith, said flap seam being between said liquid barrier and said flap elastic member.

12. The article of claim 11 wherein each said flap seam is between a respective said leg elastic member and a respective said flap elastic member.

13. The article of claim 7 wherein each said leg elastic member is in a respective said liquid barrier zone.

14. A disposable absorbent article, comprising:
   a pant body comprising a front panel, a back panel, and tearable, nonrefastenable side seams joining portions of said front panel and said back panel to define a waist opening periphery, a pair of leg opening peripheries, and an interior space,
   said pant body further comprising a liquid impermeable backsheet including a front edge, a back edge, and a pair of side edges, said front edge and said back edge being substantially contiguous with said waist opening periphery,
   a liquid permeable topsheet,
   an absorbent structure between said liquid impermeable backsheet and said liquid permeable topsheet,
   a first liquid barrier zone defined by said backsheet on one side of said absorbent structure, and a second liquid barrier zone defined by said backsheet on an other side of said absorbent,
   a liquid impermeable containment flap over each said liquid barrier zone,
   a flap seam positioned over said absorbent structure and adhering said liquid impermeable containment flap on top of said liquid permeable topsheet, and a liquid barrier in each said liquid barrier zone between said liquid impermeable containment flap and said liquid impermeable backsheet, and extending between said front edge and said back edge of said liquid impermeable backsheet.

15. The article of claim 14 wherein said backsheet comprises an outer layer and a liquid impermeable inner layer, and a leg elastic member between said outer layer and said liquid impermeable inner layer, and being elastically associated along each said side edge of said backsheet.

16. The article of claim 15 wherein each said containment flap includes a flap elastic member elastically associated therewith, and wherein each said liquid barrier is between a respective said leg elastic member and a respective said flap elastic member.

17. The article of claim 16 wherein each said liquid barrier comprises an adhesive bondline.

18. The article of claim 16 wherein each said liquid barrier comprises a thermal bondline.

19. The article of claim 16 wherein each said liquid barrier comprises an ultrasonic bondline.

20. The article of claim 15 wherein each said leg elastic member is in a respective said liquid barrier zone.

21. The article of claim 14 wherein each said liquid barrier zone has a width of about 2 millimeters or greater.

* * * * *